(12) United States Patent
Singh et al.

(10) Patent No.: US 11,207,661 B2
(45) Date of Patent: Dec. 28, 2021

(54) PROCESS TO PEPTIZE ALUMINA FOR FLUIDIZABLE CATALYSTS

(71) Applicant: W.R. GRACE & CO.—CONN., Columbia, MD (US)

(72) Inventors: Udayshankar Singh, Ellicott City, MD (US); Sundaram Krishnamoorthy, Ellicott City, MD (US); Michael Scott Ziebarth, Columbia, MD (US); Wu-Cheng Cheng, Ellicot City, MD (US)

(73) Assignee: W.R. Grace & Co.—CONN., Columbia, MD (US)

( * ) Notice: Subject to any disclaimer, the term of this patent is extended or adjusted under 35 U.S.C. 154(b) by 0 days.

(21) Appl. No.: 16/322,156

(22) PCT Filed: Jul. 25, 2017

(86) PCT No.: PCT/US2017/043698
§ 371 (c)(1),
(2) Date: Jan. 31, 2019

(87) PCT Pub. No.: WO2018/026574
PCT Pub. Date: Feb. 8, 2018

(65) Prior Publication Data
US 2019/0184375 A1    Jun. 20, 2019

Related U.S. Application Data

(60) Provisional application No. 62/369,313, filed on Aug. 1, 2016.

(51) Int. Cl.
| | | |
|---|---|---|
| *B01J 21/04* | (2006.01) | |
| *B01J 37/04* | (2006.01) | |
| *B01J 35/02* | (2006.01) | |
| *B01J 37/06* | (2006.01) | |
| *B01J 37/08* | (2006.01) | |
| *C10G 11/05* | (2006.01) | |
| *B01J 29/40* | (2006.01) | |
| *B01J 29/08* | (2006.01) | |
| *B01J 21/16* | (2006.01) | |
| *B01J 29/70* | (2006.01) | |
| *B01J 29/85* | (2006.01) | |
| *B01J 35/00* | (2006.01) | |
| *B01J 35/10* | (2006.01) | |
| *B01J 37/00* | (2006.01) | |
| *C07C 1/24* | (2006.01) | |
| *C10G 3/00* | (2006.01) | |
| *C10G 11/18* | (2006.01) | |

(52) U.S. Cl.
CPC .............. *B01J 21/04* (2013.01); *B01J 21/16* (2013.01); *B01J 29/088* (2013.01); *B01J 29/40* (2013.01); *B01J 29/7049* (2013.01); *B01J 29/85* (2013.01); *B01J 35/0026* (2013.01); *B01J 35/023* (2013.01); *B01J 35/1014* (2013.01); *B01J 35/1019* (2013.01); *B01J 37/0036* (2013.01); *B01J 37/0045* (2013.01); *B01J 37/0072* (2013.01); *B01J 37/04* (2013.01); *B01J 37/06* (2013.01); *B01J 37/08* (2013.01); *C07C 1/24* (2013.01); *C10G 3/49* (2013.01); *C10G 3/57* (2013.01); *C10G 11/05* (2013.01); *C10G 11/18* (2013.01); *B01J 2229/42* (2013.01); *C07C 2521/04* (2013.01); *C07C 2529/70* (2013.01); *C10G 2300/70* (2013.01)

(58) Field of Classification Search
CPC .... B01J 21/04; B01J 37/0045; B01J 37/0072; B01J 37/04; B01J 37/06; B01J 37/08; C10G 3/57; C10G 11/18; C07C 2524/04; C01F 7/021
See application file for complete search history.

(56) References Cited

U.S. PATENT DOCUMENTS

| | | | |
|---|---|---|---|
| 3,293,192 A | 12/1966 | Maher et al. | |
| 3,894,963 A * | 7/1975 | Gerdes | B01J 35/026 |
| | | | 502/320 |
| 4,086,187 A | 4/1978 | Lim et al. | |
| 4,179,408 A | 12/1979 | Sanchez et al. | |
| 4,440,871 A | 4/1984 | Lok et al. | |

(Continued)

FOREIGN PATENT DOCUMENTS

| | | |
|---|---|---|
| CN | 1237146 A | 12/1999 |
| CN | 102791374 A | 11/2012 |

(Continued)

OTHER PUBLICATIONS

Examination Report dated Mar. 4, 2018, issued in counterpart SA application No. GC 2017-33781. (4 pages).
Office Action dated Mar. 20, 2019, issued in counterpart EP application No. 17837404.7. (3 pages).
International Search Report dated Oct. 5, 2017, issued in counterpart International Application No. PCT/US2017/043698 (2 pages).
Written Opinion of the International Searching Authority (Form PCT/ISA/237) dated Oct. 5, 2017, issued in counterpart International Application No. PCT/US2017/043698 (8 pages).

(Continued)

*Primary Examiner* — Jun Li
(74) *Attorney, Agent, or Firm* — Foley & Lardner LLP

(57) ABSTRACT

A process for preparing a peptized alumina having increased solids and acid contents and a decreased water content. The process comprising mixing a boehmite or pseudoboehmite alumina and acid with a high intensity, high energy mixer at a ratio of 0.16 to 0.65 moles acid/moles alumina for a time period sufficient to form a substantially free-flowing solid particulate having a solids content of 45 to 65 wt %. When used in catalyst manufacture, peptized alumina produced by the process provides an increased rate in catalyst production and decreased costs due to high solids concentration and the presence of less water to be evaporated.

48 Claims, No Drawings

(56) References Cited

U.S. PATENT DOCUMENTS

| | | | |
|---|---|---|---|
| 4,443,553 | A | 4/1984 | Chiang et al. |
| 4,476,239 | A | 10/1984 | Chiang et al. |
| 4,500,651 | A | 2/1985 | Lok et al. |
| 4,544,143 | A | 10/1985 | Cooper et al. |
| 4,567,029 | A | 1/1986 | Wilson et al. |
| 4,683,217 | A | 7/1987 | Lok et al. |
| 4,686,092 | A | 8/1987 | Lok et al. |
| 4,705,767 | A | 11/1987 | Cheng et al. |
| 4,744,970 | A | 5/1988 | Lok et al. |
| 4,758,419 | A | 7/1988 | Lok et al. |
| 4,764,269 | A | 8/1988 | Edwards et al. |
| 4,793,984 | A | 12/1988 | Lok et al. |
| 4,923,843 | A | 5/1990 | Saforo et al. |
| 4,935,216 | A | 6/1990 | Lok et al. |
| 5,098,684 | A | 3/1992 | Kresge et al. |
| 5,102,643 | A | 4/1992 | Kresge et al. |
| 5,192,734 | A * | 3/1993 | Creighton ............... B01J 23/85 502/314 |
| 5,198,203 | A | 3/1993 | Kresge et al. |
| 5,866,496 | A | 2/1999 | Albers et al. |
| 6,114,267 | A | 9/2000 | Ghosh et al. |
| 6,930,067 | B2 | 8/2005 | O'Connor et al. |
| 2003/0136707 | A1 * | 7/2003 | Harris ................. B01J 35/0026 208/120.01 |
| 2005/0209093 | A1 | 9/2005 | Chester et al. |
| 2005/0238572 | A1 * | 10/2005 | Martin .................... C01F 7/026 423/626 |
| 2006/0096891 | A1 | 5/2006 | Stamires et al. |
| 2010/0252484 | A1 | 10/2010 | Kumar et al. |
| 2013/0005565 | A1 | 1/2013 | Shu et al. |
| 2014/0174983 | A1 * | 6/2014 | Klein .................... C10G 47/10 208/89 |
| 2015/0375216 | A1 | 12/2015 | Stamires et al. |

FOREIGN PATENT DOCUMENTS

| | | |
|---|---|---|
| CN | 104411402 A | 3/2015 |
| EP | 0 159 624 A2 | 10/1985 |
| EP | 0 369 171 A1 | 5/1990 |
| WO | 2007/070498 A1 | 6/2007 |
| WO | 2015/157429 A1 | 10/2015 |

OTHER PUBLICATIONS

Examination Report dated Mar. 4, 2019, issued in counterpart SA application No. GC 2017-33781. (4 pages).

Extended (Supplementary) European search Report dated Feb. 28, 2020, issued in counterpart EP Application No. 17837404.7(9 pages).

Office Action dated Jun. 29, 2021, issued in counterpart JP application No. 2019-505400, with English translation. (15 pages).

Office Action dated Jul. 28, 2021, issued in counterpart CN application No. 201780060935.0, with English translation (26 pages).

* cited by examiner

PROCESS TO PEPTIZE ALUMINA FOR FLUIDIZABLE CATALYSTS

FIELD OF THE INVENTION

The invention relates to a process for preparing a peptized alumina. More particularly, the invention relates to a process for peptizing alumina for spray-dried, fluidizable catalysts in dry, particulate form.

BACKGROUND OF THE INVENTION

Spray-dried, fluidizable catalysts are used throughout the refining industry to produce fuels or chemical building blocks or polymers. For example, such catalysts include those used in cracking processes such as Deep Catalytic Cracking (DCC) and Fluid Catalytic Cracking (FCC), as well as the so-called Methanol to Olefins (MTO) process, where methanol is converted to olefins such as ethylene and propylene. In particular, the fluid catalytic cracking unit is the primary hydrocarbon conversion unit in the modern petroleum refinery. It uses heat and catalyst to convert a variety of high molecular weight feed types (e.g., gas oils, cracked gas oils, deasphalted gas oils, and atmospheric/vacuum resids) into lighter, more valuable products such as gasoline, light fuel oil, and petrochemical feedstocks such as propylene and butylene. A key factor in the success of the FCC unit is the versatility of the FCC catalyst itself. Generally containing zeolite, an active alumina, clay and binder system, the complementary nature of the components in FCC catalyst design enable its successful use with a wide slate of petroleum refining streams. The zeolite portion of an FCC catalyst is a crystalline silica-alumina structure having pores in the range of 7.4-12 Å, where molecules smaller than 10.2 Å can enter the zeolite pores to be cracked. The active alumina portion is an amorphous silica-alumina structure having pores in the mesopore range (20-500 Å) as well as macropores (>500 Å). The zeolite is responsible for the vast majority of coke selective cracking that takes place in an FCC catalyst, however, it is obviously limited by the size of molecules that it can crack. In contrast, the active alumina does not provide cracking as coke selective as the zeolite, however, it can crack larger molecules that the zeolite cannot effectively process. As a result, there is a synergy between zeolite cracking and matrix cracking, where the matrix can "pre-crack" molecules that are too large to be cracked by the zeolite itself into a size that can be processed by the zeolite. A wide range of gasoline selectivity and octane can also be obtained by adjusting the level of rare earth exchanged into the zeolite. Thus, catalyst manufacturers and refiners can tune the particular makeup of their catalyst to optimize its design for the particular feed being processed.

Boehmite or pseudoboehmite, whether or not peptized, is sometimes used as the active alumina in FCC catalysts, or the alumina-based binder for the FCC catalysts. Peptized aluminas are also used in the manufacture of hydroprocessing catalysts, although the manner in which the aluminas are peptized is significantly different. The successful use of peptized alumina in FCC catalyst application is due in part to the excellent cracking capability of the alumina along with the presence of its relatively large pore size, i.e., the so-called mesopores. Further, peptized alumina typically possess good apparent bulk density, are a very effective binder, and produce catalyst having a larger pore size and good unit retention. The larger pore sizes provide active cracking sites in the alumina which are accessible to the molecules to be cracked, and as discussed above, acts in conjunction with the more coke selective, but size-dependent. In the case of hydrotreating catalysts, alumina provides good binding strength for pellet formation, high surface area for effective dispersion of active metal compounds and tailored pore characteristics for effective diffusion of the reactant molecules.

Typically, peptized aluminas for producing hydroprocessing catalysts are prepared using less than 0.1 mol acid/mol alumina (less than 5% acid usage), while FCC catalysts typically use greater amounts. For hydroprocessing catalysts, the lower usage of acid is important to preserve the pore size distribution and pore volume in the final catalyst and allow it to be extruded into its industrial useful form. In contrast, the FCC catalyst must be spray dried from a slurry to acquire the necessary spherical shape and properties (i.e. attrition, bulk density and surface area), required for particle fluidization.

Peptization of alumina is recognized as including the breakdown of large alumina particles to small particles, by chemical treatment, to make a suitable binder for the catalyst application. In conventional wet peptization processes, alumina is treated with acid in an aqueous slurry and aged. The process typically utilizes high amounts of aqueous acid, i.e., two times or more than the incipient wetness pore volume of alumina, and is carried out in a batch mode taking several hours to complete. The process uses a large quantity of water to keep the viscosity of the peptized alumina low so that it can be pumped to other process steps. This high amount of water limits the maximum solids content in the peptized alumina solution to typically less than 20 wt. %. When making FCC or other spray dried catalysts, the peptized alumina typically makes up 20-60 wt. % of the catalyst. If the peptized alumina raw material stream is low in solids, this leads to low catalyst spray drier feed solids content, which results in low catalyst manufacturing throughput and high energy usage.

Improvements in the peptization process, either with regard to improving catalytic performance or plant utilization (capacity), can have a substantial impact on the economics associated with the use of FCC catalyst. Consequently, work has continued in this area to optimize operations.

U.S. Pat. No. 6,930,067 discloses a process for preparing a catalyst combining catalyst components or precursors thereof in an aqueous medium to form a catalyst precursor mixture. The mixture is then fed to a shaping apparatus, to form particles, where the mixture is destabilized less than about 300 seconds before the shaping step.

U.S. Pat. No. 4,086,187 discloses an attrition resistant catalyst composition utilizing a pseudoboehmite peptized using formic acid with an acid utilization (acid/alumina) of 0.065 moles acid/moles alumina.

U.S. Pat. Nos. 4,179,408 4,179,408 discloses a process for preparing spheroidal alumina particles where the alumina is peptized using a wet peptization process in a slurry having a pH of 4.0 to 4.8, at an acid/alumina molar ratio of 0.03 to 0.5.

U.S. Pat. Nos. 4,443,553 and 4,476,239 disclose processes for preparation of fluid catalyst cracking catalysts wherein the viscosity of an aqueous slurry containing a zeolite, an alumina containing binder, clay and a silica source can be significantly reduced by incorporation of a small amount of aluminum hydroxychloride or aluminum hydroxynitrate respectively.

U.S. Pat. No. 5,866,496 discloses a process for manufacturing a fluid cracking catalyst wherein (1) the order of addition of ingredients in the catalyst slurry is modified to have the inorganic acid used for peptization added prior to the addition of the pseudoboehmite component and (2) a phosphrous-containing dispersant is added in an amount from 0.05 wt % to about 0.6 wt % to enable an increase in the solids content of the spray dryer feed slurry.

Nevertheless, there is an ongoing need for processes that improve the efficiency, capacity and run rate of the FCC manufacturing plant. It has unexpectedly been found that the inventive process described in the present disclosure increases plant throughput while maintaining good catalyst properties.

SUMMARY OF THE INVENTION

The essence of the present invention resides in the discovery of a process for producing peptized alumina having increased solids and acid content simultaneously with a decreased water content, and processes for producing spray-dried, fluidized catalysts using the peptized alumina. Advantageously, the higher concentration of acid increases the manufacturing rate of the peptized alumina and eliminates the need for ageing. When used for catalyst production, the peptized alumina produced using the process of the invention provides an increased catalyst production rate due to the high concentration of solids in the peptized alumina. The process of the invention also provides decreased costs during catalyst manufacture due to the use of less energy. In one embodiment, the present disclosure provides a process for preparing peptized alumina comprising mixing a boehmite alumina and acid at a ratio of 0.16 to 0.65 moles acid/moles alumina for a period of time with a mixer having an energy and an intensity sufficient to form a substantially free-flowing solid particulate having a solids content of about 45 to about 65 wt %. In a preferred embodiment, the boehmite alumina and acid are mixed at a ratio sufficient to provide a pH of 2.5 to 4.0 when the resulting free-flowing solid particulate is slurried or dispersed in an aqueous solution having a solids concentration of 20 wt %.

In another embodiment, the present disclosure provides a process for producing a spray-dried, fluidizable catalyst comprising combining the free-flowing, peptized alumina particulate produced in accordance with the present disclosure, with a zeolite and water to form a spray dryer feed, and then spray-drying the spray dryer feed to provide a catalyst.

DETAILED DESCRIPTION OF THE INVENTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise.

"About" modifying, for example, the concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

As used herein, the term "boehmite" include the term "pseudoboehmite" and is used to indicate a solid alumina material of formula $Al_2O_3.H_2O$ and having an x-ray diffraction pattern of which shows broad lines that coincide with the major reflections of well crystallized $\gamma$-AlOOH, having crystallites sizes ranging from about 20 to about 1000 Å. Consequently, for purposes of this disclosure, the terms "bohemite" and "pseudoboehmite" will be used herein interchangeably.

As used herein, the term "fluidizable" means generally spherical, spray-dried solid particles having an average particle size of 20 to 150µ, an apparent bulk density of 0.65 to 1.2 $g/cm^3$, and a 0-40µ fraction of the catalyst particles being between 0-30 volume %.

As used herein, the term "free-flowing" is used to indicate a non-sticky solid having no free liquid, which flows as solid particles.

As used herein, the term "peptized" or "peptization" is used to indicate the formation of a stable dispersion of alumina particles in an acid medium.

As used herein, the term "pore size" is used to indicate the diameter of the pores.

As used herein, the term "substantially" means within a reasonable amount, but includes amounts which vary from about 0% to about 50% of the absolute value, from about 0% to about 40%, from about 0% to about 30%, from about 0% to about 20% or from about 0% to about 10%.

Peptizing Process

The inventive process relates to a process for peptizing aluminas for use in fluidizable catalysts. Generally, the process described in the current specification utilizes an aqueous acidic solution amount that is less than the alumina incipient wetness pore volume, to make a solid particulate peptized alumina. This produces peptized alumina with a solids content of about 45 to about 65%. The concentration of acid is higher due to less water, which speeds up the peptization reaction and eliminates the need for aging. The higher peptized alumina solids concentration and faster peptization results in a higher manufacturing rate of the peptized alumina and the potential to use a much smaller reaction vessel. When used for catalyst production, the higher peptized alumina solids concentration leads to a higher catalyst spray dryer feed solids concentration which results in a higher catalyst production rate. Energy usage is also lower due to less water evaporation during spray drying.

In accordance with the present disclosure, the boehmite alumina is peptized by acidifying it in an aqueous medium. The acid and alumina are typically used in an amount of about 0.16 to about 0.65 moles acid per mole of alumina, preferably, the acid and boehmite alumina are used in an amount of about 0.20 to about 0.50 moles acid/moles alumina. More preferably, the acid and boehmite alumina are used in an amount of about 0.25 to about 0.45 moles acid/moles alumina. Most preferably, the acid and boehmite alumina are used in amounts of about 0.3 to about 0.40 moles acid/moles alumina.

The acid used to peptize the alumina is any acid suitable to form a stable dispersion of alumina particles. In one embodiment the acid is selected from monoprotic acids. More preferably, the acid is selected from the group consisting of formic acid, nitric acid, hydrochloric acid, acetic acids, and mixtures thereof. Even more preferably, the acid used to peptize the alumina is hydrochloric or nitric acid.

Mixing of the boehmite alumina with acid according to the present disclosure results in a peptized alumina that is a substantially free-flowing particulate solid. Preferably, the solid particulate has a liquid content below the incipient wetness point, i.e., the point at which pore volume saturation is achieved.

Batch and Continuous Processes

The peptized aluminas can be produced by either batch or continuous processes. When produced in a batch process, the alumina can be prepared in any suitable reactor(s) or open vessel(s) that can accommodate the reaction streams. Boehmite alumina, water and acid as described above are routed to the batch vessel, where the initial temperature is from about 40° F. to about 100° F., preferably, about 60° F. to about 90° F. The temperature of the alumina increases during the peptization due to the heat of reaction and the heat input due to mixing, so that the maximum temperature during the reaction is about 130° F. to about 200° F., preferably, about 150° F. to about 180° F. The mixing time for the batch mixing process is preferably 0.1 to 5.0 hours, more preferably, about 0.5 to about 3.0 hours, and even more preferably, about 1.0 to about 2.0 hours.

When the peptized aluminas are produced in a continuous process, the alumina can be prepared in any suitable reactor or open vessel that can accommodate the reaction stream. Preferably, the reactor is jacketed to allow heating or cooling. Boehmite alumina, water and acid are mixed in the vessel at initial and maximum temperatures as described above. Mixing times for the continuous process is preferably less than 10 minutes, more preferably, from about 1.0 to about 5.0 minutes, and even more preferably from about 2.0 to about 3.0 minutes.

For both the batch and continuous processes, the mixing system used in the reactor is a mixing system having an intensity and energy sufficient to form a substantially free-flowing particulate solid. In one embodiment, the mixing system is a high intensity mixing system, where for the purposes of this specification, the term "high intensity mixing system" means a system that delivers from about $5.0 \times 10^{-4}$ to about 0.1 horsepower*hr/lb-peptized solid mixture. In another embodiment of the invention, the mixer system is one that delivers about 0.001 to about 0.05 horsepower*hr/lb-peptized solid mixture. Preferably, when a batch process is used, the reactor can be a rotating type, such as that manufactured by Eirich Machines or a stationary type like a Sigma or Mikrons mixer, and utilizes a vertical mixer impeller. When a continuous process is used, the mixer impeller can be a vertical impeller or a horizontal shaft-paddle assembly. Examples of the continuous mixer include those manufactured by Readco Kurimoto Inc., Leistritz Corporation, and Littleford Day. Preferably, in the continuous process, the mixers feature a single or twin shaft design with mixing elements such as paddles or screws designed in a specific configuration to impart high mechanical energy input. Preferably, the high intensity mixer is a continuous mixer of the horizontal type, equipped with close clearances between the paddles and the barrel wall to provide more efficient and uniform mixing in shorter duration than batch mixers.

Peptized Solid Particulate Properties

Typically, the average particle size of the peptized alumina solid particulate material formed by the process of the invention is less than 200μ, preferably less 100μ. In an embodiment, the average particle size of the peptized alumina formed by the process of the invention ranges from about 1μ to about 200μ, preferably from about 3μ to about 100μ, most preferably from about 5μ to about 30μ. In an even more preferable embodiment, the average particle size of the peptized alumina particulate produced by the invention process is about 10μ to about 15μ. The average particle size is measured by ASTM D4464.

The apparent bulk density of the peptized alumina solid particulate formed in accordance with the process of the invention is from about 0.3 to about 2.0 g/cm$^3$. In a preferred embodiment, the apparent bulk density is from 0.4 to 1.0 g/cm$^3$, and more preferably, from 0.5 to 0.8 g/cm$^3$. The apparent bulk density is measured by ASTM D1895.

The peptized alumina solid particulate produced by the process of the invention has a solids content of about 45.0 to about 65.0 wt %, measured as total volatiles at 1750° F. for 1 hour. In one embodiment of the invention, the solids content of the peptized alumina solid particulate is about 47.0 wt % to about 62.0 wt % based on the total weight of the solid particulates. In a preferred embodiment, the solids content of the peptized alumina solid particulate is about 50.0 wt % to about 60.0 wt % based on the total weight of the solid particulates. The Al$_2$O$_3$ content of the peptized alumina solid particulate ranges from about 80 to about 100 wt %, preferably, from about 90 to about 100 wt % based on the total weight of the solid particulates.

Slurried pH of Particulate Solids

The solids resulting from the peptization process disclosed herein are free-flowing, non-sticky with no free liquid. However, if slurried to form a solution, the pH of the resulting solution is a measure of the unreacted free acid in the solution, which in turn is an indication of the acid takeu$_p$ of the alumina. Such a slurry is prepared by slurrying the peptized alumina solids with water at a concentration of 20 wt % solids. Water at room temperature is used, and a standard glass electrode probe is used to measure the pH. Prior to the measurement, the probe is calibrated with buffer solutions at pH 4.0 and pH 7.0, at room temperature. When slurried at a concentration of 20 wt % solids, the peptized solids preferably have a pH of 2.5 to 4.0. More preferably, the resulting slurry has a pH of 2.75 to 3.75, and even more preferably, a pH of 3 to 3.5.

Catalyst

The peptized alumina can be incorporated in spray-dried, fluidizable catalysts. Such catalysts are suitable for transport in, e.g., an FCC reactor standpipe. Preferably, the fluidizable catalyst is selected from DCC, MTO or FCC catalysts. Even more preferably, the catalyst is an FCC catalyst comprising a zeolite, the peptized alumina, clay, binder, and optionally added silica and other matrix material.

Zeolite/Molecular Sieve

The Molecular sieve used in the fluidizable catalyst can be any molecular sieve typically used in DCC, MTO or FCC catalysts, which include, but are not limited to, Y-zeolites, ZSM-5 zeolites, SAPO or ALPO molecular sieves, or mixtures thereof. When the fluidizable catalyst contains a SAPO molecular sieve, the SAPO molecular sieve is preferably SAPO-34. When the fluidizable catalyst is an FCC catalyst, the zeolite utilized in the FCC catalyst can be any zeolite having catalytic activity in a hydrocarbon conversion process. Generally, the zeolites can be large pore size zeolites that are characterized by a pore structure with an opening of at least 0.7 nm and medium or small pore size zeolites having a pore size smaller than 0.7 nm, but larger than about 0.40 nm. Suitable large pore zeolites are described further below. Suitable medium pore size zeolites include pentasil zeolites such as ZSM-5, ZSM-22, ZSM-23, ZSM-35, ZSM-50, ZSM-57, MCM-22, MCM-49, MCM-56 all of which are known materials.

Suitable large pore zeolites comprise crystalline aluminosilicate zeolites such as synthetic faujasite, i.e., type Y zeolite, type X zeolite, and Zeolite Beta, as well as heat treated (calcined) derivatives thereof. Zeolites that are particularly suited include ultrastable type Y zeolite (USY) as disclosed in U.S. Pat. No. 3,293,192. The zeolite may also be blended with molecular sieves such as SAPO and ALPO as disclosed in U.S. Pat. No. 4,764,269.

Preferably, the zeolite is a Y-type zeolite. Zeolites useful in the invention also include zeolites that have been pre-exchanged with a rare earth. Also rare earths can be added to the zeolite during spray drying to produce the catalyst or post-treatment of the zeolite containing particle, i.e. by adding a rare earth compound, e.g. rare earth salt, into a spray drier feed containing the Y-type zeolite, or by treating the spray dried Y-type zeolite particle with a rare earth containing solution. Preferably, the rare earth is present in an amount from about 0.0 to about 8.0 wt %, more preferably about 1.0 to about 6.0 wt % based on the total weight of the catalyst.

Standard Y-type zeolite is commercially produced by crystallization of sodium silicate and sodium aluminate. This zeolite can be converted to USY-type by dealumination, which increases the silicon/aluminum atomic ratio of the parent standard Y zeolite structure. Dealumination can be achieved by steam calcination or by chemical treatment.

The unit cell size of a preferred fresh Y-zeolite is about 24.45 to about 24.7 Å. The unit cell size (UCS) of zeolite can be measured by X-ray analysis under the procedure of ASTM D3942. Although both the zeolite, per se, and the matrix of a fluid cracking catalyst usually contain both silica and alumina, the $SiO_2/Al_2O_3$ ratio of the catalyst matrix should not be confused with that of the zeolite. Catalyst surface area corresponding to the zeolite, i.e., surface area corresponding to pores in the range of <20 Å, preferably ranges from 20 to 300 $m^2/g$, more preferably from 60 to 200 $m^2/g$.

For purposes of this invention, the term "zeolite" is used herein to also include non-zeolitic sieves materials. Exemplary non-zeolitic sieve materials which may present in the fluidizable catalysts include silicates (such as the metallosilicates and titanosilicates) of varying silica-alumina ratios, metalloaluminates (such as germaniumaluminates), metallophosphates, aluminophosphates such as the silico- and metalloaluminophosphates referred to as metal integrated aluminophosphates (MeAPO and ELAPO), metal integrated silicoaluminophosphates (MeAPSO and ELAPSO), silicoaluminophosphates (SAPO), gallogerminates and combinations of these. A discussion on the structural relationships of SAPO's, AlPO's, MeAPO's, and MeAPSO's may be found in a number of resources including Stud. Surf. Catal. 37 13-27 (1987). The AlPO's contain aluminum and phosphorus, whilst in the SAPO's some of the phosphorus and/or some of both phosphorus and aluminum is replaced by silicon. In the MeAPO's various metals are present, such as Li, B, Be, Mg, Ti, Mn, Fe, Co, An, Ga, Ge, and As, in addition to aluminum and phosphorus, whilst the MeAPSO's additionally contain silicon. The negative charge of the $Me_aAl_bP_cSi_dO_e$ lattice is compensated by cations, where Me is magnesium, manganese, cobalt, iron and/or zinc. $Me_xAPSOs$ are described in U.S. Pat. No. 4,793,984. SAPO-type sieve materials are described in U.S. Pat. No. 4,440,871; MeAPO type catalysts are described in U.S. Pat. Nos. 4,544,143 and 4,567,029; ELAPO catalysts are described in U.S. Pat. No. 4,500,651 and ELAPSO catalysts are described in European Patent Application 159,624. Specific molecular sieves are described, for example, in the following patents: MgAPSO or MAPSO-U.S. Pat. No. 4,758,419. MnAPSO-U.S. Pat. No. 4,686,092; CoAPSO-U.S. Pat. No. 4,744,970; FeAPSO-U.S. Pat. No. 4,683,217 and ZnAPSO U.S. Pat. No. 4,935,216. Specific silicoaluminophosphates which may be used include SAPO-11, SAPO-17, SAPO-34, SAPO-37; other specific sieve materials include MeAPO-5, MgAPSO-5.

Another class of crystalline materials which may be used is the group of mesoporous crystalline materials exemplified by the MCM-41 and MCM-48 materials. These mesoporous crystalline materials are described in U.S. Pat. Nos. 5,098,684; 5,102,643; and 5,198,203. MCM-41, which is described in U.S. Pat. No. 5,098,684, is characterized by a microstructure with a uniform, hexagonal arrangement of pores with diameters of at least about 1.3 nm: after calcination it exhibits an X-ray diffraction pattern with at least one d-spacing greater than about 1.8 nm and a hexagonal electron diffraction pattern that can be indexed with a d100 value greater than about 1.8 nm which corresponds to the d-spacing of the peak in the X-ray diffraction pattern. The preferred catalytic form of this material is the aluminosilicate although other metallosilicates may also be utilized. MCM-48 has a cubic structure and may be made by a similar preparative procedure.

Generally, the zeolite component comprises from about 5 wt % to about 50 wt % of the cracking catalyst. Preferably, the zeolite component comprises from about 12 wt % to about 40 wt % of the total catalyst composition.

Matrix

The catalyst can also include active matrix in addition to the peptized alumina discussed above. This is catalytically active, porous silica-alumina material, however, in contrast to the zeolite, it is non-crystalline, i.e., amorphous. The active matrix contains pores in the mesopore range (about 20 to about 500 Å) as well as macropores (>500 Å). Surface area corresponding to the matrix, i.e., the surface of pores in the catalyst in the range of from about 20 to about 10000 Å, ranges from about 10 to about 250 $m^2/g$, preferably from about 60 to about 200 $m^2/g$, more preferably, about 80 to about 150 $m^2/g$, and even preferably, about 90 to about 100 $m^2/g$ prior to deactivation. Suitable additional matrix materials are selected from the group consisting of non-peptized alumina, zirconia, titania, and combinations thereof. The matrix material may be present in the inventive catalyst in an amount ranging from about 1 wt % to about 70 wt % of the total catalyst composition.

The total surface area of the catalyst is preferably about 30 to about 450 $m^2/g$, more preferably, about 120 to about 350 $m^2/g$, prior to deactivation, as determined by the Brunauer, Emmett and Teller (BET) method.

Clay

The FCC catalyst also includes clay. While not generally contributing to the catalytic activity, clay provides mechanical strength and density to the overall catalyst particle to enhance its fluidization. While kaolin is the preferred clay component, it is also contemplated that other clays, such as modified kaolin (e.g. metakaolin) may be optionally included in the invention catalyst. The clay component will typically comprise from about 5 wt % to about 80 wt % of the total weight of the catalyst composition, preferably from about 25 wt % to about 55 wt % of the total weight of the catalyst composition.

Added Silica

Added silica components useful in the FCC catalyst of the present subject matter may be any siliceous oxide used as a component of the matrix or added separately as a component in the form of a solid, slurry or sol. The term "added silica" does not include a siliceous oxide present in any clay, binder or zeolite component of the catalyst. In one embodiment, the added silica component comprises a silica component which includes, but is not limited to, precipitated silica, silica gel, colloidal silica, or combinations thereof. It is also within the scope of the present subject matter that the added silica component will include silica contained in a particulate silica alumina provided, however, that the silica alumina comprise greater than 60 wt % silica, preferably, greater than 75 wt % silica, most preferably greater than 80 wt % silica, based on the total weight of the silica alumina. Typically, the added silica component is present in the catalyst compositions of the present disclosure in an amount sufficient to provide at least about 2 wt % silica based on the total weight of the catalyst composition. In one embodiment, the added silica component is present in the catalyst in an amount sufficient to provide from about 2 to about 20 wt %, and preferably from about 3 to about 10 wt %, silica based on the total weight of the catalyst composition.

Binder

The peptized alumina particulate solid described above is present as a binder. Optionally, secondary binders may also be present. Suitable secondary binders include inorganic oxides, such as alumina, silica, silica-alumina, aluminum phosphate, as well as other metal-based phosphates known in the art. Silica sols such as Ludox® colloidal silica available from W. R. Grace & Co.-Conn. and ion exchanged water glass are also suitable binders. Certain secondary binders, e.g., those formed from binder precursors, e.g., aluminum chlorohydrol, are created by introducing solutions of the binder's precursors into the mixer, and the binder is then formed upon being spray dried and/or further processed. Preferably, the secondary inorganic binder materials useful to prepare compositions in accordance with the present subject matter include, but are not limited to, alumina sol, silica alumina containing less than 50 wt % silica, or mixtures thereof. More preferably, the secondary binder is alumina sol.

Catalyst Preparation Process

The FCC catalyst of the present invention is produced by forming a homogeneous or substantially homogeneous aqueous slurry which contains the peptized alumina, a catalytically active zeolite component, a binder, clay, and optionally an added silica component and/or other active aluminas. The final catalyst composition can comprise about 5 to about 50 wt % of the catalytically active zeolite component, about 2 wt % to about 30 wt % of an added silica component, about 5 wt % to about 60 wt % of the peptized alumina particulate solid as binder, from about 5 wt % to about 80 wt % of clay, and optionally, about 1 wt % to 70 wt % of matrix material, including other active alumina matrices, and optional binders described above; said weight percentages being based on the total catalyst composition. Preferably, the aqueous slurry is milled to obtain a homogeneous or substantially homogeneous slurry, i.e. a slurry wherein all the solid components of the slurry have an average particle size of less than 10 μm. Alternatively, the components forming the slurry may be milled prior to forming the slurry. The aqueous slurry is thereafter mixed to obtain a homogeneous or substantially homogeneous aqueous slurry.

Spray Drying

The aqueous slurry may be dried using any conventional drying technique suitable to form particles. In a preferred embodiment, the slurry is spray dried to form particles having an average particle size in the range of about 20 to about 200μ, preferably, in the range of about 50 to about 100μ. The inlet temperature of the spray dryer can be in the range of about 220° C. to about 540° C., and the outlet temperature in the range of about 130° C. to about 180° C.

Calcination

The spray dried catalyst is then ready as a finished catalyst "as is", or it may be calcined for activation prior to use to remove volatiles. The catalyst particles, for example, can be calcined at temperatures ranging from about 250° C. to about 800° C. for a period of about 10 seconds to about 4 hours. Preferably, the catalyst particles are calcined at a temperature of about 350° C. to about 600° C. for about 10 seconds to about 2 hours.

The calcined catalyst has an apparent bulk density, as measured by ASTM D4512, from about 0.65 to about 1.122 g/cm$^3$. Preferably, the $Al_2O_3$ content of the calcined catalyst is about 35.0 to about 70.0 wt %, preferably, about 45.0 to about 60.0 wt % based on the total weight of the catalyst.

Washing

Optionally, the catalyst may be washed to remove excess alkali metals, which are known contaminants to catalysts, especially FCC catalysts. The catalyst can be washed one or more times, preferably with water, ammonium hydroxide, and/or aqueous ammonium salt solutions, such as ammonium sulfate solution.

The washed catalyst is separated from the wash slurry by conventional techniques, e.g. filtration, and dried to lower the moisture content of the particles to a desired level, typically at temperatures ranging from about 100° C. to about 300° C. One embodiment comprises drying the catalyst using flash drying.

The inventive method for producing peptized alumina for incorporation into catalysts results in a material having physical properties such as surface areas and apparent bulk density, as well as performance activities/selectivities, that are consistent with those made using conventional wet peptization techniques, while increasing production capacity and resulting in excellent catalyst attrition characteristics. Increased production capacity is gained because of the higher solids content of the peptized alumina being fed to the spray drier and the resultant reduced water-removal load. Improved attrition characteristics is typically quantified as a lower DI. DI refers to the Davison Attrition Index, which is an attrition resistance measurement known in the art. Briefly, the DI is defined as the quantity of <20μ fines generated over a certain period of time. To determine the Davison Attrition Index (DI) of the invention, 7.0 cc of sample catalyst is screened to remove particles in the 0 to 20μ range. Those remaining particles are then contacted in a hardened steel jet cup having a precision-bored orifice through which an air jet of humidified (60%) air is passed at 21 liter/minute for 1 hour. The DI is defined as the percent of 0-20μ fines generated during the test relative to the amount of >20μ material initially present, i.e., the formula below:

DI=100*(wt % of 0-20μ material formed during test)/(wt of original greater than 20μ before test).

Typically, the DI of FCC catalysts produced according to the present disclosure are less than 20, preferably, less than 15. Even more preferably, the DI ranges from 1 to 10, and most preferably, from 3 to 8.

To further illustrate the present invention and the advantages thereof, the following specific examples are given. The examples are given as specific illustrations of the claimed invention. It should be understood, however, that the invention is not limited to the specific details set forth in the examples. Those skilled in the art will recognize many variations that are within the spirit of the invention and scope of the claims.

All parts and percentages in the examples as well as the remainder of the specification which refers to solid compositions or concentrations are by weight unless otherwise specified. However, all parts and percentages in the examples as well as the remainder of the specification referring to gas compositions are molar or by volume unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited.

EXAMPLES

Comparative Example 1

Standard preparation of wet peptized alumina: A dilute solution of HCl was prepared by mixing 1625 g of 37% HCl with 16138 g of DI water. 7500 g of a pseudoboehmite/Boehmite alumina, crystallite size 35 Å, moisture content 30% was re-slurred with the above diluted HCl solution in a 10 gallon tank, with agitation. The slurry (targeting an acid/alumina peptization mole ratio of 0.35) was aged overnight. The resulting wet peptized alumina had the following properties: pH 2.8 at room temperature, and solids content of 20 wt %. A typical solid content for the wet peptized alumina prepared using this recipe is less than 22 wt %.

Example 2

Batch mode peptization of dry particulate alumina: 3000 g of pseudoboehmite/Boehmite alumina, used in Comparative Example 1, was added to a mixture of 836 g of 37% HCl and 4 g of DI water in a 1 gallon batch Eirich Mixer. It was then mixed for 90 min. A 0.35 acid/alumina peptization mole ratio was used. The resulting free-flowing peptized alumina solid particulate had the following properties: pH 3.3 (after re-slurry at 20% solids in water at room temperature), solids content of 55 wt %. A typical solid content for the dry particulate peptized alumina prepared using this recipe is between 45 to 60 wt %.

Example 3

Continuous mode peptization of dry particulate alumina: The pseudoboehmite/boehmite alumina, used in Comparative Example 1, was fed through a 5 inch Readco twin-screw continuous mixer at 12 lbs/min using a loss-in weight feeder. Hydrochloric acid, 32 wt % was fed into the mixer at a total rate of 3.3 lbs/min targeting an acid/alumina peptization molar ratio of 0.35. In addition, water was added to the mixer at a rate of 1.41 lbs/min. The resulting free-flowing peptized alumina solid particulate had the following properties: pH 3.5 (after re-slurry at 20% solids in water at room temperature), solids content of 50 wt %. A typical solids content for the dry particulate peptized alumina is between 45 to 60 wt %.

Comparative Example 4

An aqueous slurry containing 1145 g (dry basis) of washed USY zeolite, 389 g of Rare earth chloride solution (105 g on a dry basis of $La_2O_3$), 8334 g (1500 g dry basis) of the wet peptized alumina from Example 1, 750 g (300 g dry basis) of colloidal silica, and 2295 g (1950 g dry basis) of Kaolin Clay were mixed in a high shear Myers mixer for 10 minutes. The mixture was milled to reduce particle size, and spray dried in a Bowen spray dryer at a solid content of 32 wt % (measured at 955° C.). The spray dried particles were calcined, washed to lower $Na_2O$, and dried in oven at 132° C. overnight. This was designated as Comparative Catalyst A, and its properties are listed in Table 1.

Example 5

An aqueous slurry containing 1145 g (dry basis) of washed USY zeolite, 389 g of Lanthanum salt solution (105 g on a dry basis of $La_2O_3$), 2727 g (1500 g dry basis) of particulate peptized alumina from Example 2, 750 g (300 g dry basis) of colloidal silica, and 2295 g (1950 g dry basis) of Kaolin Clay were mixed in a high shear Myers mixer for 10 minutes. The mixture was milled to reduce particle size, and spray dried in a Bowen spray dryer at a solid content of 40 wt % (measured at 955° C.). The spray dried particles were calcined, washed to lower $Na_2O$, and dried in oven at 132° C. overnight. This was designated as Catalyst B and its properties are listed in Table 1.

The higher spray dryer feed solids of ~40% (vs. ~32 wt % by standard process) achieved by the new inventive process provides an increase in catalyst production rate of ~42%, compared to standard wet peptization process (Table 2). This is mainly due to evaporating less water in the spray dryer at a constant feed rate.

The data in Table 1 shows fresh properties Comparative Catalyst A and Catalyst B formulated with different spray dryer feed solid levels has similar properties.

TABLE 1

Fresh properties of Catalyst A and Catalyst B.

|  | Comparative Catalyst A | Catalyst B (high spray dryer feed solids - "SDF") |
|---|---|---|
| Spray dryer feed Solids, wt % | 32 | 40 |
| Apparent Bulk Density, g/cm³ | 0.69 | 0.69 |
| Attrition Index (DI) | 6 | 6 |
| Zeolite Surface Area, m²/g | 147 | 167 |
| Matrix Surface Area, m²/g | 139 | 143 |
| Total Surface Area, m²/g | 286 | 310 |
| $Al_2O_3$, %: | 52.1 | 51.6 |
| $Na_2O$, %: | 0.17 | 0.17 |
| $RE_2O_3$, %: | 2.2 | 2.3 |

TABLE 2

Benefits of High Spray Dryer Feed Solids

|  | Standard Comparative catalyst | Catalyst from High SDF Solids | Benefits of Invention |
|---|---|---|---|
| Spray Dryer Feed Solids, % | 32 | 40 | |
| Amount of water to be evaporated, per 100 g | 68 | 60 | |

TABLE 2-continued

Benefits of High Spray Dryer Feed Solids

|  | Standard Comparative catalyst | Catalyst from High SDF Solids | Benefits of Invention |
|---|---|---|---|
| g of catalyst produced per g of water evaporated | 0.471 | 0.667 |  |
| Rate increase, % |  |  | ~42% |

If manufacturing is limited due to the Spray Dryer (amount of water to be evaporated) then the catalyst production rate will increase by ~42%

Example 6

Deactivation and Performance Testing of Comparative Catalyst A and Catalyst B

To determine the stability of Comparative Catalyst A and Catalyst B for FCC application, the Catalysts were impregnated with 2000 ppm Ni and 3000 ppm V and then steam deactivated using Cyclic Propylene Steam (CPS) protocol at 788° C., as described in Lori T. Boock, Thomas F. Petti, and John A. Rudesill, *ACS Symposium Series,* 634, 1996, 171-183. The analyses of steamed properties show that both catalysts have similar Unit Cell Size, but Catalyst B has significantly higher surface area, both fresh and after deactivation (Table 1 and 3).

TABLE 3

Deactivated properties of Comparative Catalyst A and Catalyst B.

|  | Comparative Catalyst A | Catalyst B (high SDF solids) |
|---|---|---|
| Zeolite Surface Area, m²/g | 76 | 87 |
| Matrix Surface Area, m²/g | 96 | 94 |
| Total Surface Area, m²/g | 172 | 181 |
| Unit Cell Size, A | 24.31 | 24.31 |
| Nickel, ppm | 2060 | 2025 |
| Vanadium, ppm | 3250 | 3230 |

DCR Performance Testing of Comparative Catalyst A and Catalyst B:

Performance testing was done in Davison Circular Riser (DCR) at a reactor temperature of 538° C., as described in G. W. Young, G. D. Weatherbee, and S. W. Davey, "Simulating Commercial FCCU Yields with the Davison Circulating Riser Pilot Plant Unit," National Petroleum Refiners Association (NPRA) Paper AM88-52. For DCR testing the deactivated versions of Comparative Catalyst A and Catalyst B, from Example 4 and 5, were used. The interpolated yields at a constant conversion of 71 wt % are shown in Table 4. The data shows that Catalyst B, formulated with dry particulate peptized alumina, has similar performance as that of Comparative Catalyst A, formulated with standard wet peptized alumina.

TABLE 4

DCR performance testing: Interpolated Yields at a constant conversion of 71 wt %.
At Constant Conversion of 71 wt %

|  | Comparative Catalyst A | Catalyst B (High SDF Solids) |
|---|---|---|
| Catalyst-to-Oil Ratio | 8.4 | 8.6 |
| Dry gas, Wt % | 2.7 | 2.7 |

TABLE 4-continued

DCR performance testing: Interpolated Yields at a constant conversion of 71 wt %.
At Constant Conversion of 71 wt %

|  | Comparative Catalyst A | Catalyst B (High SDF Solids) |
|---|---|---|
| Total LPG, wt % | 15.3 | 15.2 |
| Gasoline, Wt % | 47.7 | 47.7 |
| LCO, Wt % | 21.3 | 21.1 |
| Bottoms, Wt % | 7.7 | 7.9 |
| Coke, Wt % | 5.3 | 5.4 |

Example 7

Effect of Peptization Ratio on Catalyst Binding Properties

To explore the effect of peptization ratio on catalyst binding properties, dry particulate peptized alumina was prepared with different acid-to-alumina mole ratios in a batch Eirich Mixer. The dry particulate aluminas were prepared as described in Example 2. The acid inputs were adjusted to achieve peptization mole ratios of 0.15, 0.25, 0.35 and 0.45. All samples were prepared at a solids content of ~50 wt %. The samples are labeled as solid Particulate Peptized Aluminas Al-1, Al-2, Al-3, and Al-4, respectively. Table 5 lists the properties of particulate peptized alumina. The data shows that the alumina surface area decreases with increase in the peptization ratio.

TABLE 5

Properties of dry Particulate Peptized Alumina Al-1, Al-2, Al-3 and Al-4.

|  | Particulate Peptized Al-1 | Particulate Peptized Al-2 | Particulate Peptized Al-3 | Particulate Peptized Al-4 |
|---|---|---|---|---|
| Peptization ratio, mol acid/mol Al₂O₃ | 0.15 | 0.25 | 0.35 | 0.45 |
| Total Volatiles at 955° C., wt % | 45 | 48 | 50 | 48 |
| Surface Area, m²/g | 355 | 348 | 282 | 285 |

Example 8

Catalyst C was made using the same procedure as that for Catalyst B described in Example 5 except that Particulate Peptized Alumina Al-1 (peptization ratio 0.15) was used.

Example 9

Catalyst D was prepared using the same procedure as that for Catalyst B described in Example 5 except that Particulate Peptized Alumina Al-2 (peptization ratio 0.25) was used.

Example 10

Catalyst E was prepared using the same procedure as that for Catalyst B described in Example 5 except that solid Particulate Peptized Alumina Al-3 (peptization ratio 0.35) was used.

Example 11

Catalyst F was prepared using the same procedure as that for Catalyst B described in Example 5 except that solid Particulate Peptized Alumina Al-4 (peptization ratio 0.45) was used.

The properties of Catalysts C to F are shown in Table 6. It has been observed that higher peptization ratio is preferred to make catalyst with good binding properties. The data shows a peptization ratio of greater than 0.15 is necessary to make a catalyst with acceptable attrition of DI<20.

TABLE 6

Fresh properties of Catalysts formulated with dry particulate alumina with different peptization ratios.

| Property | Units | Catalyst C | Catalyst D | Catalyst E | Catalyst F |
|---|---|---|---|---|---|
| Acid/Alumina Peptization ratio, | mol acid/mol $Al_2O_3$ | 0.15 | 0.25 | 0.35 | 0.45 |
| Apparent Bulk Density | g/cc | 0.63 | 0.64 | 0.73 | 0.74 |
| Attrition Index DI | — | 21 | 15 | 6 | 6 |
| Zeolite Surface Area | m$^2$/g | 162 | 178 | 180 | 172 |
| Matrix Surface Area | m$^2$/g | 136 | 125 | 119 | 115 |
| Total Surface Area | m$^2$/g | 298 | 303 | 299 | 287 |
| $Al_2O_3$ | wt % | 52.8 | 53.4 | 53.6 | 52.1 |
| $Na_2O$ | wt % | 0.21 | 0.20 | 0.19 | 0.20 |
| $RE_2O_3$ | wt % | 2.2 | 2.2 | 2.2 | 2.1 |

Comparative Example 12

Comparative Catalyst G was prepared using the method described in Comparative Example 4. The spray dryer feed solid for catalyst in this example was at 32 wt %. Properties of Comparative Catalyst G are listed in Table 7.

Example 13

Catalyst H was prepared using the same procedure as that for Catalyst B, as described in Example 5, except that the alumina used was from Example 3. The spray dryer feed solids achieved for this was ~40 wt %, which provides increase in catalyst production rate of ~42%, compared to standard wet peptization process. This is mainly due to evaporating less water in the spray dryer at a constant feed rate. The properties of Catalysts H compared against the Comparative Catalyst G are listed in Table 7. Analyses of Physical and chemical properties show the two catalysts have similar properties. The data concludes that the use of a dry peptization process, to peptize alumina, results in final catalyst with similar properties as compared to the catalyst prepared by alumina peptized by wet process, peptized alumina, but at higher production rate.

TABLE 7

Fresh properties of Comparative Catalysts G and Catalyst H.

| Property | Units | Catalyst G | Catalyst H |
|---|---|---|---|
| Apparent Bulk Density | g/cm$^3$ | 0.73 | 0.74 |
| Attrition Index DI | — | 7 | 4 |
| Zeolite Surface Area | m$^2$/g | 162 | 169 |
| Matrix Surface Area | m$^2$/g | 126 | 126 |
| Total Surface Area | m$^2$/g | 288 | 295 |
| $Al_2O_3$ | wt % | 50 | 49.8 |
| $Na_2O$ | wt % | 0.21 | 0.17 |
| Rare Earth Oxides | wt % | 2.1 | 2.2 |

Example 14

Deactivation and Performance Testing of Comparative Catalyst G and Catalyst H

To determine the stability of Comparative Catalyst G and Catalyst H for FCC application, the Catalysts were impregnated with 2000 ppm Ni and 3000 ppm V and then steam deactivated using Cyclic Propylene Steam protocol at 788° C. The analyses of steamed properties show that both catalysts have similar Unit Cell Size, but Catalyst H formulated with dry peptized alumina has higher surface, both fresh and after deactivation (Table 7 and 8).

TABLE 8

Deactivated properties of Catalysts G and Catalyst H.

| Properties | Units | Catalyst G | Catalyst H |
|---|---|---|---|
| Zeolite Surface Area | m$^2$/g | 83 | 88 |
| Matrix Surface Area | m$^2$/g | 83 | 83 |
| Total Surface Area | m$^2$/g | 166 | 172 |
| Unit Cell Size | Å | 24.31 | 24.30 |
| Nickel | ppm | 2040 | 2010 |
| Vanadium | ppm | 3300 | 3330 |

ACE Performance Testing of Comparative Catalyst G and Catalyst H:

Performance testing was done in Advanced Cracking Evaluation (ACE) reactor at a temperature of 538° C., as described in U.S. Pat. 6,069,012. The reactor used for evaluation was an ACE Model AP Fluid Bed Microactivity unit from Kayser Technology, Inc. For ACE testing the deactivated versions of Comparative Catalyst G and Catalyst H, from Example 12 and 13, were used. The interpolated yields at a constant conversion of 71 wt % are shown in Table 9. The data shows that Catalyst H, formulated with dry particulate peptized alumina, has similar performance as that of Comparative Catalyst G, formulated with standard wet peptized alumina. The results are consistent with Example 6 and shows that the catalysts prepared from alumina peptized by dry process has properties and performance similar to the alumina prepared by wet process.

TABLE 9

ACE performance testing: Interpolated Yields at a constant conversion of 71 wt %.
At Constant Conversion of 71 wt %

| | Catalyst G | Catalyst H |
|---|---|---|
| Cat-to-Oil Ratio | 6.3 | 6.6 |
| Total Dry Gas, wt % | 2.2 | 2.2 |
| Total LPG, wt % | 14.2 | 14.2 |
| Gasoline, wt % | 48.7 | 48.7 |
| LCO, wt % | 22.2 | 22.1 |
| Bottoms, wt % | 6.8 | 6.9 |
| Coke, wt % | 5.9 | 5.9 |

Example 15

ZSM 5 Based Catalyst Formulated with Particulate Peptized Alumina

An aqueous slurry containing 4000 g (dry basis) of washed ZSM-5 zeolite, 1780 g of Phosphoric acid (1096 g on a dry basis of $P_2O_5$), 2727 g (1200 g dry basis) of particulate peptized alumina from Example 2, 3478 g (800 g dry basis) of colloidal alumina, and 1064 g (904 g dry basis)

of Kaolin Clay were mixed in a high shear Myers mixer for 10 minutes. The mixture was milled to reduce particle size, and spray dried in a Bowen spray dryer at a solid content of 34 wt % (measured at 955° C.). The spray dried particles were calcined and designated as Catalyst I. Properties of this catalyst is listed in Table 10.

Analyses of Physical and chemical properties show that the Particulate Peptized Alumina can be used to make a ZSM-5 based catalyst with good attrition properties and low $Na_2O$. The ZSM-5 based catalyst can be used in DCC or FCC applications or in any other process where ZSM-5 catalysts are utilized.

TABLE 10

| Properties | Units | Catalyst I ZSM-5 Based Catalyst |
|---|---|---|
| Attrition Index (DI) | | 6 |
| Zeolite Surface Area | $m^2/g$ | 172 |
| Matrix Surface Area | $m^2/g$ | 43 |
| Total Surface Area | $m^2/g$ | 215 |
| $Al_2O_3$ | wt % | 31.5 |
| $Na_2O$ | wt % | 0.1 |
| $RE_2O_3$ | wt % | 0.01 |
| $P_2O_5$ | wt % | 13.5 |

Example 16

SAPO 34 Based Catalyst Formulated with Particulate Peptized Alumina

An aqueous slurry containing 3100 g (dry basis) of washed SAPO 34, 3822 g (1860 g dry basis) of particulate peptized alumina from Example 2, 2696 g (620 g dry basis) of colloidal alumina, and 730 g (620 g dry basis) of Kaolin Clay were mixed in a high shear Myers mixer for 10 minutes. The mixture was milled to reduce particle size, and spray dried in a Bowen spray dryer at a solid content of 38 wt % (measured at 955° C.). The spray dried particles were calcined and designated as Catalyst J. Properties of this catalyst is listed in Table 11.

Analyses of Physical and chemical properties show that the Particulate Peptized Alumina can be used to make a SAPO 34 based catalyst with good attrition properties and low $Na_2O$. The SAPO-34 based catalyst can be used in MTO process applications or in any other process where SAPO-34 catalysts are utilized.

TABLE 11

| Properties | Units | Catalyst J SAPO 34 Based Catalyst |
|---|---|---|
| Attrition Index (DI) | | 14 |
| Zeolite Surface Area | $m^2/g$ | 275 |
| Matrix Surface Area | $m^2/g$ | 117 |
| Total Surface Area | $m^2/g$ | 392 |
| $Al_2O_3$ | wt % | 62.5 |
| $Na_2O$ | wt % | 0.1 |
| $RE_2O_3$ | wt % | 0.00 |
| $P_2O_5$ | wt % | 25.0 |

We claim:

1. A process comprising:
mixing a porous boehmite alumina with an aqueous acid solution at a ratio of about 0.16 to about 0.65 moles acid/moles alumina for a time period and with a mixer having a sufficient energy and intensity to form a free-flowing peptized alumina solid particulate having liquid content below the incipient wetness point and having a solids content of about 45 to about 65 wt %, measured as total volatiles at 1750° F. for 1 hour; wherein an amount of the aqueous acid solution is less than the alumina incipient wetness pore volume.

2. The process of claim 1 wherein the free-flowing solid particulate has a pH of 2.5 to 4.0 when slurried in an aqueous solution at a concentration of 20 wt % solids.

3. The process of claim 1 wherein the ratio acid to alumina is from about 0.20 to about 0.50 moles acid/moles alumina.

4. The process of claim 1 wherein the solids content of the free-flowing solid particulate is 47 to 62 wt %.

5. The process of claim 1 wherein the process is a batch process.

6. The process of claim 1 wherein the process is a continuous process.

7. The process of claim 6 wherein the time period is less than 10 minutes.

8. The process of claim 1 wherein the ratio is 0.20 to 0.50 moles acid/moles alumina.

9. The process of claim 8 wherein the ratio is 0.25 to 0.45 moles acid/moles alumina.

10. The process of claim 9 wherein the ratio is 0.3 to 0.40 moles acid/moles alumina.

11. The process of claim 4 wherein the solids content of the free-flowing peptized alumina solid particulate is from 50 to 60 wt %.

12. The process of claim 1 wherein the mixer is a high intensity mixer for delivering $5.0 \times 10^{-4}$ to 0.1 horsepower*hr/lb-peptized solid mixture.

13. The process of claim 12 wherein the high intensity mixer delivers 0.001 to 0.05 horsepower*hr/lb-peptized solid mixture.

14. The process of claim 2 wherein the pH of the slurry solution is from 2.75 to 3.75.

15. The process of claim 14 wherein the pH of the slurry solution is from 3.0 to 3.5.

16. The process of claim 1 wherein the free-flowing peptized alumina solid particulate has an alumina content from about 80.0 to about 100 wt. % based on the total weight of the peptized alumina solid particulate.

17. The process of claim 1 wherein the free-flowing solid particulate has an average particle size of about 1 to about 200 μm.

18. The process of claim 17 wherein the average particle size is from about 5 to about 20 μm.

19. The process of claim 1 wherein the free-flowing solid particulate has an apparent bulk density of about 0.3 to about 2.0 $g/cm^3$.

20. The process of claim 19 wherein the apparent bulk density of about 0.4 to about 1.0 $g/cm^3$.

21. The process of claim 20 wherein the apparent bulk density of about 0.5 to about 0.8 $g/cm^3$.

22. A process for producing a fluidizable catalyst comprising:
(a) mixing a porous boehmite or porous pseudoboehmite alumina and acid at a ratio of about 0.16 to about 0.65 moles acid/moles alumina for a time period and with a mixer having a sufficient intensity and energy, to form a free-flowing peptized alumina solid particulate having liquid content below the incipient wetness point and having a solids content of 45 to 65 wt %; wherein an amount of the aqueous acid solution is less than the alumina incipient wetness pore volume
(b) combining the peptized alumina solid particulate with zeolite and water to form a spray dryer feed; and (c) spray-drying the spray-dryer feed to form a spray-dried fluidizable catalyst.

23. The process of claim 22 wherein the catalyst is an FCC catalyst, a DCC catalyst or an MTO catalyst.

24. The process of claim 22 wherein the free-flowing peptized alumina solid particulate of step (a) has a pH of about 2.5 to about 4.0 when slurried in an aqueous solution having a concentration of 20 wt % solids.

25. The process of claim 24 wherein the pH of the slurry solution is from about 2.75 to about 3.75.

26. The process of claim 22 wherein the solids content of the free-flowing solid particulate of step (a) is 47.0 to 57.0 wt %.

27. The process of claim 22 wherein the process is a batch process.

28. The process of claim 22 wherein the process is a continuous process.

29. The process of claim 28 further comprising that the mixing of step (a) continues for a time period of less than 10 minutes.

30. The process of claim 22 wherein the ratio is about 0.20 to about 0.50 moles acid/moles alumina.

31. The process of claim 30 wherein the ratio is about 0.25 to about 0.45 moles acid/moles alumina.

32. The process of claim 31 wherein the ratio is about 0.3 to about 0.40 moles acid/moles alumina.

33. The process of claim 26 wherein the solids content of the free-flowing peptized alumina solid particulate is from about 50.0 to about 60.0 wt %.

34. The process of claim 22 wherein the mixer is a high intensity mixer for delivering $5.0 \times 10^{-4}$ to 0.1 horsepower*hr/lb-peptized solid mixture.

35. The process of claim 34 wherein the high intensity mixer delivers 0.001 to 0.05 horsepower*hr/lb-peptized solid mixture.

36. The process of claim 22 wherein the combining step further comprises combining clay.

37. The process of claim 22 wherein the zeolite comprises rare earth.

38. The process of claim 22 wherein the spray-drying step is conducted at a spray dryer outlet temperature of about 130 to about 180° C.

39. The process of claim 22 further comprising calcining the spray-dried fluidizable catalyst at a temperature of about 250° C. to about 800° C.

40. The process of claim 22 wherein the free-flowing peptized alumina solid particulate has an alumina content of about 80.0 to about 100.0 wt % based on the weight of the peptized alumina particulate.

41. The process of claim 23 wherein the FCC catalyst has a rare earth level of about 0.0 to about 6.0 wt %, based on the weight of the catalyst.

42. The process of claim 23 wherein the FCC catalyst has a total surface area of about 30 to about 450 $m^2/g$.

43. The process of claim 23 wherein the FCC catalyst has a zeolite surface area of about 20 to about 300 $m^2/g$.

44. The process of claim 23 wherein the FCC catalyst has a matrix surface area of about 10 to about 150 $m^2/g$.

45. The process of claim 23 wherein the FCC catalyst has an apparent bulk density of about 0.4 to about 0.8 $g/cm^3$.

46. The process of claim 23 wherein the fluidizable catalyst is an FCC catalyst.

47. The process of claim 22 wherein the zeolite is selected from ZSM-5, Y-zeolite, SAPO or mixtures thereof.

48. The process of claim 47 wherein the SAPO zeolite is SAPO-34.

* * * * *